(12) United States Patent
Carruthers et al.

(10) Patent No.: US 9,283,512 B2
(45) Date of Patent: *Mar. 15, 2016

(54) ADSORBENT HAVING UTILITY FOR $CO_2$ CAPTURE FROM GAS MIXTURES

(71) Applicant: Entegris, Inc., Billerica, MA (US)

(72) Inventors: J. Donald Carruthers, Fairfield, CT (US); Melissa A. Petruska, Newtown, CT (US); Shaun M. Wilson, Trumbull, CT (US); Edward A. Sturm, New Milford, CT (US)

(73) Assignee: ENTEGRIS, INC., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/833,225

(22) Filed: Aug. 24, 2015

(65) Prior Publication Data

US 2015/0360164 A1 Dec. 17, 2015

Related U.S. Application Data

(62) Division of application No. 13/857,385, filed on Apr. 5, 2013.

(51) Int. Cl.
*B01D 53/02* (2006.01)
*B01D 53/04* (2006.01)
(Continued)

(52) U.S. Cl.
CPC .............. *B01D 53/04* (2013.01); *B01J 20/20* (2013.01); *B01J 20/28011* (2013.01);
(Continued)

(58) Field of Classification Search
CPC ................ B01D 2253/102; B01D 2253/202; B01D 2253/304; B01D 2253/308; B01D 2253/311; B01D 2256/245; B01D 2257/504; B01D 2258/05; B01D 53/02; B01D 53/0462; B01D 53/0476; B01D 53/053; B01D 53/62; B01J 20/20; B01J 20/28011; B01J 20/28016; C01B 31/08; C12M 47/18; Y02C 10/04; Y02C 10/08; Y10T 428/2982

See application file for complete search history.

(56) References Cited

U.S. PATENT DOCUMENTS 4,046,709 A 9/1977 Yuki
5,071,820 A 12/1991 Quinn et al.
(Continued)

FOREIGN PATENT DOCUMENTS

EP 1064996 A1 1/2001
JP 2003-535803 A 12/2003
(Continued)

OTHER PUBLICATIONS

Jan. 28, 2015 Office Action issued in U.S. Appl. No. 13/857,385 by Christopher P. Jones.
(Continued)

*Primary Examiner* — Christopher P Jones
(74) *Attorney, Agent, or Firm* — Hultquist IP; Steven J. Hultquist

(57) ABSTRACT

A carbon pyrolyzate adsorbent is described that is selective for carbon dioxide in contact with gas mixtures including carbon dioxide and methane. The adsorbent has a carbon dioxide adsorbent capacity at 1 bar pressure of greater than 50 $cm^3$ carbon dioxide per gram of adsorbent at 273K, a methane adsorption capacity at 1 bar pressure of less than 35 $cm^3$ methane per gram of adsorbent at 21° C., and a bulk density of greater than 0.55 gram per cubic centimeter of volume. Such adsorbent can be utilized, for example, for biogas upgrading, natural gas purification, coal bed methane purification, and refining operations.

34 Claims, 4 Drawing Sheets

(51) Int. Cl.
  *B01J 20/30* (2006.01)
  *B01J 20/28* (2006.01)
  *B01J 20/20* (2006.01)

(52) U.S. Cl.
  CPC ....... *B01J 20/28016* (2013.01); *B01J 20/3078* (2013.01); *B01D 2253/102* (2013.01); *B01D 2256/245* (2013.01); *B01D 2257/504* (2013.01)

(56) References Cited

U.S. PATENT DOCUMENTS

| | | |
|---|---|---|
| 5,518,528 A | 5/1996 | Tom et al. |
| 5,614,459 A | 3/1997 | Mondragon et al. |
| 5,704,965 A | 1/1998 | Tom et al. |
| 5,704,967 A | 1/1998 | Tom et al. |
| 5,707,424 A | 1/1998 | Tom et al. |
| 5,935,305 A | 8/1999 | Tom et al. |
| 5,993,766 A | 11/1999 | Tom et al. |
| 6,030,698 A | 2/2000 | Burchell et al. |
| 6,309,446 B1 | 10/2001 | Nakanoya et al. |
| 6,475,461 B1 | 11/2002 | Ohsaki et al. |
| 6,670,039 B1 | 12/2003 | Nagle |
| 6,743,278 B1 | 6/2004 | Carruthers |
| 6,939,394 B2 | 9/2005 | Carruthers |
| 6,991,671 B2 | 1/2006 | Brestovansky et al. |
| 7,455,719 B2 | 11/2008 | Carruthers |
| 7,494,530 B2 | 2/2009 | Carruthers |
| 7,501,010 B2 | 3/2009 | Brestovansky et al. |
| 7,972,421 B2 | 7/2011 | Brestovansky et al. |
| 8,002,880 B2 | 8/2011 | Carruthers |
| 8,282,714 B2 | 10/2012 | Carruthers |
| 2003/0157014 A1 | 8/2003 | Wang et al. |
| 2004/0107838 A1 | 6/2004 | Carruthers |
| 2009/0038477 A1 | 2/2009 | Abe et al. |
| 2009/0258782 A1 | 10/2009 | Gogotsi et al. |
| 2009/0304570 A1 | 12/2009 | Kim et al. |
| 2010/0116136 A1 | 5/2010 | Wojtowicz et al. |
| 2010/0142122 A1 | 6/2010 | Tanaka |
| 2012/0024157 A1 | 2/2012 | Maheshwary et al. |
| 2012/0180660 A1 | 7/2012 | Wilson et al. |
| 2012/0325850 A1 | 12/2012 | Carruthers |
| 2014/0298992 A1 | 10/2014 | Carruthers et al. |

FOREIGN PATENT DOCUMENTS

| | | |
|---|---|---|
| JP | 2006-7127 A | 1/2006 |
| WO | 9744118 A1 | 11/1997 |
| WO | 9747382 A1 | 12/1997 |
| WO | 0224310 A1 | 3/2002 |
| WO | 02068324 A1 | 9/2002 |
| WO | 2009011750 A2 | 1/2009 |
| WO | 2012106218 A2 | 8/2012 |
| WO | 2012145337 A1 | 10/2012 |

OTHER PUBLICATIONS

Mar. 6, 2015 Office Action issued in U.S. Appl. No. 13/857,385 by Christopher P. Jones.

Bagreev, A., et al., "Desulfurization of digester gas: prediction of activated carbon bed performance at low concentrations of hydrogen sulfide", "Catalysis Today", Dec. 15, 2004, pp. 329-337, vol. 99.

Jimenez-Cruz, F., et al., "Adsorption of n-Heptane and 2-Methylheptane in the Gas Phase on Polyvinylidene Chloride-Based Microporous Activated Carbon", "Energy and Fuels", Aug. 17, 2007, pp. 2929-2934, vol. 21.

Jung, H., et al., "Pore Structure Characterization of Poly(vinylidene chloride)-Derived Nanoporous Carbons", "Carbon Letters", Oct. 31, 2012, pp. 236-242, vol. 13, No. 4.

Xu, B., et al., "An Activation-Free Method for Preparing Microporous Carbon by the Pyrolysis of Poly(Vinylidene Fluoride)", "Carbon", Apr. 14, 2010, pp. 2812-2814, vol. 48.

ADSORBENT HAVING UTILITY FOR $CO_2$ CAPTURE FROM GAS MIXTURES

CROSS-REFERENCE TO RELATED APPLICATION

This is a divisional application under the provisions of 35 U.S.C. §120 of U.S. patent application Ser. No. 13/857,385 filed Apr. 5, 2013. The disclosure of U.S. patent application Ser. No. 13/857,385 is hereby incorporated herein by reference in its entirety, for all purposes.

FIELD

The present disclosure relates to an adsorbent material that is useful for adsorptive removal of carbon dioxide from gas mixtures containing carbon dioxide in combination with other gases, e.g., natural gas containing carbon dioxide, biogas from anaerobic digestion processes, coal bed methane, and output gas mixtures from steam-methane-reforming processes. The disclosure additionally relates to $CO_2$ capture apparatus utilizing such adsorbent material and to methods of using the adsorbent.

DESCRIPTION OF THE RELATED ART

Natural gas, composed primarily of methane, is ubiquitous as a fuel source.

Trends and projections of sustained growth in global population, accompanied by increased generation of waste and consumption of energy reinforce the necessity to conserve natural resources and to convert waste back into a renewable energy source. Around the world there is plentiful supply of biogas sources, including fermented sewage, municipal waste, livestock manure, and general biomass. The composition of the biogas available from these sources is primarily methane ($CH_4$) at typically 60 to 90% and carbon dioxide ($CO_2$) at approximately 10 to 40%, with a variety of other components present in lesser concentrations depending upon the specific source. Conversion of these available gases to fuel energy is an attractive and green alternative to continued waste and atmospheric release, particularly in light of the greenhouse impact of these gases. In order for the biogas to be utilized as a replacement for natural gas, it typically must be upgraded to ≤97% $CH_4$, (<3% $CO_2$), with other restrictions placed on trace impurities depending on utility company guidelines and local regulations.

In addition to its utility as a fuel, methane is employed in a number of chemical processes.

In such applications, significant concentrations of gas components other than methane, e.g., carbon dioxide, hydrogen sulfide, ammonia, water, siloxanes, etc. may pose problems. For example, many combustion processes employed to manufacture glass and ceramics are sensitive to the BTU content of fuel, and variations attributable to the presence of carbon dioxide or gas components other than methane can create severe process and quality issues. In application to chemical processes, significant concentrations of carbon dioxide result in lower yields of ultimate products if the $CO_2$ is present as a major contaminant in the methane being used as a reactant.

Furthermore, shipment of natural gas is necessary for distribution and has become commonplace on a transcontinental and intercontinental scale. For such shipment, it is desirable to minimize all non-methane contaminants in the natural gas, so that extraneous components are not being unnecessarily shipped in the large volumes of natural gas being transported. It therefore is desirable to remove carbon dioxide from the methane in such applications.

Around the globe, those currently involved in upgrading biogas mixtures employ a variety of technologies to increase the methane concentration in their gas streams including: water scrubbing, chemical absorption, chemical scrubbing, cryogenic separation, membrane separations, and pressure swing adsorption. Each approach has its associated advantages and shortcomings.

Water scrubbing is currently the most popular separation technique and takes advantage of the higher aqueous solubility of $CO_2$ versus $CH_4$ to preferentially remove $CO_2$ from the methane/$CO_2$ mixture when contacted with water. This can be a relatively high flow rate and low cost approach to upgrading the methane concentration but since the solubility of $CO_2$ in the water can vary significantly with changing temperature, system performance can differ from site to site. $CO_2$ solubility in water improves greatly at lower temperatures and higher pressures but maintaining these conditions adds significant cost and size to the system. Additionally, since the water dissolves other contaminants such as $H_2S$ or $NH_3$, the pH of the water can change and cause varying effectiveness in $CO_2$ capture. This approach also requires handling and neutralization of great volumes of water and drying of the effluent methane before use.

Chemical scrubbing can be performed at close to atmospheric pressure due to the use of engineered chemicals such as amine solutions with much higher $CO_2$ capacities than water. Typically these chemical solutions are regenerated by addition of heat to drive off the captured $CO_2$. Though the systems can often be designed and constructed at lower cost and smaller size than water scrubbing systems, there is a higher energy cost in regeneration.

Chemical adsorption uses specially designed materials to react with the contaminants to be captured or to catalyze their breakdown. This approach is used quite regularly and effectively for removal of $H_2S$ contaminants in natural gas sources. One of the drawbacks with this approach is that typically a separate column is required for each targeted contaminant and the catalysts or chemicals can be expensive and often they cannot be regenerated and have a short life cycle. This creates much waste for disposal from the process.

Cryogenic separation takes advantage of the different boiling points and vapor pressures of the gases in the mixture to separate the desired species from the contaminants, but this is harder to do effectively at high flow rates and therefore requires large storage vessels and gas handling equipment able to withstand the associated temperature cycles and pressures. As a result, this approach can be quite capital intensive.

Membrane separation provides gas purification by use of precision engineered membranes that allow the passage of certain gas molecules while preventing that of others. Typically the $CO_2$, water, and ammonia are allowed to permeate while the methane is retained and thereby concentrated. The membranes can be fairly costly, and this approach normally must be paired with another technique such as chemical absorption for removal of the $H_2S$. Additionally, the retained methane is typically only concentrated to approximately 90% and must often go through an additional pressure swing adsorption step to raise the concentration above 97%. Furthermore, the yields from such processes only approach 50-70%.

Pressure swing adsorption (PSA) is a mature technology and the second most common approach to enriching methane gas sources at this time. This approach utilizes specialty porous solid adsorbents which selectively adsorb $CO_2$ much more readily than they do $CH_4$. Well-tuned PSA systems can give high methane yields and very high purity. The effluent methane stream is typically relatively dry and free of significant water vapor. This technology can be readily adaptable to different climates, different feed sources, and different scales. The energy demands for regeneration of the PSA adsorbent beds are variable and depend upon the particular adsorbent used, but can be quite low in comparison to a number of the other approaches.

The solid adsorbent is the fundamental component of the PSA system approach. These adsorbents are typically selected from among a vast commercial supply of zeolites, activated carbons, carbon molecular sieves (CMS), and specialty designed aluminosilicates and titanosilicates. Many of these adsorbents are susceptible to poisoning in the presence of $H_2S$ or physically degrade over time due to moisture in the gas streams. Properties of the adsorbent are critical to the determination of the cost of operating a PSA system. It is desirable for the adsorbent to exhibit high volumetric adsorption capacity for $CO_2$, high selectivity of $CO_2$ over $CH_4$, low heat of adsorption to enable low energy regeneration, high kinetic rates of adsorption for $CO_2$ at relatively low pressures to minimize bed size and pressure requirements, physical stability in the environment of use, and insensitivity to the various contaminants in the feed stream to enable long service life to be achieved.

SUMMARY

The present disclosure relates to an adsorbent material with utility for adsorptive removal of carbon dioxide from gas mixtures containing same, such as gas mixtures containing carbon dioxide in combination with methane, e.g., natural gas containing carbon dioxide, biogas from anaerobic digestion processes, coal bed methane, and output gas mixtures from steam-methane-reforming processes. The disclosure additionally relates to methods of using such adsorbent material for $CO_2$ capture and removal from gas mixtures, and to apparatus designed for utilizing such adsorbent for $CO_2$ capture and removal methods.

The disclosure relates in one aspect to an adsorbent material that is selective for carbon dioxide in contact with gas mixtures including carbon dioxide and methane, such adsorbent having a carbon dioxide adsorption capacity at 1 bar pressure of greater than 50 $cm^3$ carbon dioxide per gram of adsorbent at 273K, a methane adsorption capacity at 1 bar pressure of less than 35 $cm^3$ methane per gram of adsorbent at 21° C., and a bulk density of greater than 0.55 gram per cubic centimeter of volume.

In another aspect, the disclosure relates to an adsorbent, e.g., a carbon pyrolyzate adsorbent, which is selective for carbon dioxide in contact with gas mixtures including carbon dioxide and methane. Such adsorbent exhibits the following properties:
  i) total ash content of less than 1%, preferably ≤0.7%, most preferably ≤0.5% as measured by ASTM D2866
  ii) bulk density, as measured by ASTM D2854, of greater than 0.55 g/cc and less than 1.25 g/cc, preferably >0.60 g/cc and <1.15 g/cc, most preferably >0.65 g/cc and <1.00 g/cc
  iii) carbon dioxide adsorption capacity measured at 1 bar pressure and a temperature of 273 Kelvin of greater than 50 $cm^3$ carbon dioxide per gram of adsorbent, preferably >75 cc/g, and most preferably >85 cc/g
  iv) methane adsorption capacity measured at 1 bar pressure and a temperature of 21° C. of less than 35 $cm^3$ methane per gram of adsorbent, preferably <30 cc/g, and most preferably <20 $cm^3$/g
  v) $CO_2$ heats of adsorption and desorption each of which is in the range of 5 to 50 kJ/mole, preferably in the range of 10 to 40 kJ/mole, most preferably 10 to 35 kJ/mole
  vi) single pellet radial crush strength for a nominal 3 mm pellet of greater than 7 kilopound (kP), preferably >9 kP, most preferably ≥11 kP as measured by ASTM D4179.

In a further aspect, the disclosure relates to a method of making a carbon pyrolyzate adsorbent with the above characteristics (i)-(vi), such method comprising pyrolyzing a polymer or copolymer of polyvinylidene fluoride or polyvinylidene chloride to form a pyrolyzate, and activating the pyrolyzate under sufficient conditions of environment, pressure, temperature, and time to yield the carbon pyrolyzate adsorbent having the characteristics (i)-(vi).

Another aspect of the disclosure relates to an apparatus for removing carbon dioxide from a gas mixture including carbon dioxide and methane. Such apparatus comprises at least one adsorbent bed of carbon pyrolyzate adsorbent that is selective for carbon dioxide in contact with the gas mixture. The carbon pyrolyzate adsorbent has a carbon dioxide adsorbent capacity at 1 bar pressure of greater than 50 $cm^3$ carbon dioxide per gram of adsorbent, a methane adsorption capacity at 1 bar pressure of less than 35 $cm^3$ methane per gram of adsorbent, and a bulk density of greater than 0.55 gram per cubic centimeter of volume. The at least one adsorbent bed is arranged (i) for contacting with the gas mixture during a first period of time to adsorb carbon dioxide on the carbon pyrolyzate adsorbent in the bed, and discharge from the bed a carbon dioxide-reduced methane gas, and (ii) for desorbing previously adsorbed carbon dioxide from the carbon pyrolyzate adsorbent in the bed during a second period of time. The adsorbent in such apparatus may comprise a carbon adsorbent having the aforementioned characteristics (i)-(vi).

In a further aspect, the disclosure relates to a method of removing carbon dioxide from a gas mixture including carbon dioxide and methane, such method comprising contacting the gas mixture with a carbon pyrolyzate adsorbent having a carbon dioxide adsorbent capacity at 1 bar pressure of greater than 50 $cm^3$ carbon dioxide per gram of adsorbent at 273K, a methane adsorption capacity at 1 bar pressure of less than 35 $cm^3$ methane per gram of adsorbent at 21° C., and a bulk density of greater than 0.55 gram per cubic centimeter of volume. Such method may be carried out using a carbon adsorbent having the above-mentioned characteristics (i)-(vi).

Other aspects, features and embodiments of the disclosure will be more fully apparent from the ensuing description and appended claims.

DETAILED DESCRIPTION

Figure 1:
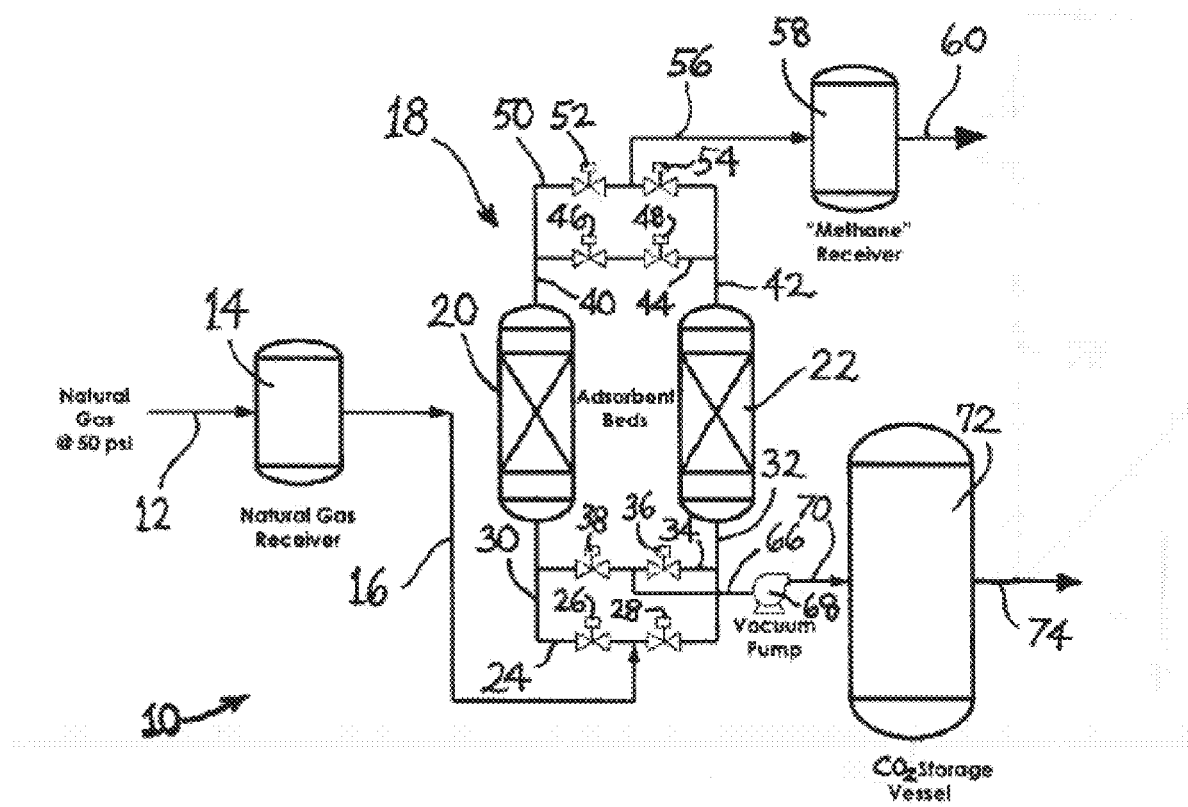
FIG. 1 is a schematic representation of a process system for removing carbon dioxide from natural gas containing carbon dioxide, according to one embodiment of the present disclosure.

As used herein and in the appended claims, the singular forms "a", "and", and "the" include plural referents unless the context clearly dictates otherwise.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure correspondingly contemplates such features, aspects and embodiments, or a selected one or ones thereof, in various permutations and combinations, as being within the scope of the present disclosure.

The present disclosure relates to an improved adsorbent material and use of such adsorbent material in apparatus and methods for the adsorptive removal of carbon dioxide from gas mixtures including carbon dioxide and methane, e.g., natural gas, biogas, coal bed methane, syngas, etc., containing carbon dioxide as an undesired contaminant of such gas mixture.

The present disclosure reflects the discovery of a carbon adsorbent, e.g., a carbon pyrolyzate adsorbent, which is usefully employed to separate carbon dioxide from gas mixtures containing carbon dioxide and methane. Adsorptive separation of carbon dioxide/methane gas mixtures has been considered very difficult, in consequence of the very close sizes of the respective carbon dioxide and methane molecules—methane has a molecular size of 0.38 nm and carbon dioxide has a molecular size of 0.32 nanometers (MIN1 dimensions).

As discussed more fully hereinafter, the adsorbent of the present disclosure is highly selective for carbon dioxide over methane. It relies not solely on physical segregation of the gas molecules based on molecular size, but rather enhances that selectivity via favorable kinetics for $CO_2$ physical adsorption and the exclusion of $CH_4$ capture. In addition to the yield enhancement value of excluding methane during adsorption of $CO_2$ from $CO_2$/methane gas mixtures, the adsorbent of the present disclosure has the additional benefit that by excluding methane from adsorption, the heat of adsorption associated with methane capture is eliminated or minimized. Such exclusion of methane thereby serves to keep the adsorbent, and beds of adsorbent containing same, cooler than would be the case if methane adsorption were occurring simultaneously with $CO_2$ adsorption.

The adsorbent of the disclosure in various embodiments comprises an adsorbent material that is selective for carbon dioxide in contact with gas mixtures including carbon dioxide and methane. Such adsorbent has a carbon dioxide adsorption capacity at 1 bar pressure of greater than 50 $cm^3$ carbon dioxide per gram of adsorbent at 273K, a methane adsorption capacity at 1 bar pressure of less than 35 $cm^3$ methane per gram of adsorbent at 21° C., and a bulk density of greater than 0.55 gram per cubic centimeter of volume.

In various embodiments, the adsorbent has the following characteristics: (i) total ash content of less than 1%, preferably ≤0.7%, most preferably ≤0.5% as measured by ASTM D2866, e.g., an ash content that is in a range of from 0.05% to 0.5%; (ii) bulk density, as measured by ASTM D2854, of greater than 0.55 g/cc and less than 1.25 g/cc, preferably >0.60 g/cc and <1.15 g/cc, most preferably >0.65 g/cc and <1.00 g/cc; (iii) carbon dioxide adsorption capacity measured at 1 bar pressure and a temperature of 273 Kelvin of greater than 50 cm3 carbon dioxide per gram of adsorbent, preferably >75 cc/g, and most preferably >85 cc/g, e.g., a carbon dioxide adsorption capacity at 1 bar pressure of greater than 50 $cm^3$ and up to 200 $cm^3$ or more carbon dioxide per gram of adsorbent at 273K; (iv) methane adsorption capacity measured at 1 bar pressure and a temperature of 21° C. of less than 35 $cm^3$ methane per gram of adsorbent, preferably <30 cc/g, and most preferably <20 cm3/g, e.g., a methane adsorption capacity in a range of from 0.05 $cm^3$ to 30 $cm^3$ at such temperature and pressure conditions; (v) CO2 heats of adsorption and desorption each of which is in the range of 5 to 50 kJ/mole, preferably in the range of 10 to 40 kJ/mole, most preferably 10 to 35 kJ/mole; (vi) single pellet radial crush strength for a nominal 3 mm pellet of greater than 7 kilopounds (kP), preferably >9 kP, most preferably ≥11 kP as measured by ASTM D4179, e.g., in a range of from 10 to 25 kilopounds.

The adsorbent of the disclosure may be of any suitable form, and may in specific embodiments have a form selected from among monolith, block, brick, bar, disc, columnar, honeycomb, channeled block, fibrous wool, felt, fabric, sponge, mat, particulate, tablet, pellet, extrudate, and bead forms. Preferred forms in specific implementations may include particulate, tablet, pellet, bead, and extrudate forms. Particulate forms of the adsorbent may have any suitable particle size. In various embodiments, the particulate adsorbent comprises adsorbent particles of particle size in a range of 0.1 to 7.0 mm.

The porosity of the adsorbent of the present disclosure may be of any suitable character that imparts selectivity for carbon dioxide over methane. In various embodiments, the carbon pyrolyzate adsorbent includes porosity in which at least 60% of the surface area is within pores having pore size in a range of from 0.30 nm to 0.40 nm, preferably with a pore size distribution focused near 0.36 nanometers.

The adsorbent of the present disclosure, e.g., a carbon pyrolyzate adsorbent having the characteristics (i)-(vi) discussed hereinabove, may be made pyrolyzing a polymer or copolymer to form a pyrolyzate and activating the pyrolyzate under sufficient conditions of environment, pressure, temperature, and time to yield the adsorbent, e.g., a carbon pyrolyzate adsorbent having such characteristics (i)-(vi).

The pyrolysis is carried out to carbonize to pyrolyze the pyrolyzable starting material and form a carbon pyrolyzate adsorbent, at suitable process conditions and for sufficient time to achieve the desired properties, including selectivity for carbon dioxide over methane when both are present in a gas mixture contacted with the adsorbent. The process conditions, including temperature, pressure, duration, atmosphere, etc. are readily determined within the skill in the art based on the disclosure herein, to achieve the adsorbent of the present disclosure. Such determination may involve preparation of pyrolyzates of the starting material as processed at successively varying conditions to establish a set of process conditions that yields the adsorbent material of the desired character.

In general, the adsorbent may be formed as a pyrolyzate of any suitable starting material that is pyrolyzable to form the adsorbent of the disclosure. The starting material subjected to pyrolysis is advantageously an organic resin, such as a fluoro- or chloro-carbon polymer or copolymer, a hydrocarbon resin, etc. Such carbon pyrolyzate adsorbent may comprise a non-graphitizing hard carbon having narrow slit-shaped micropores. The adsorbent may for example comprise a pyrolyzate of polyvinylidene fluoride (PVDF), polyvinylidene chloride (PVDC), or a copolymer of polyvinylidene fluoride or polyvinylidene chloride with acrylonitrile, styrene, methyl acrylate, vinyl fluoride, vinyl chloride, or methyl methacrylate. Potential starting materials include, among others, polymers and copolymers available commercially under the trade names: Saran® (Dow Chemical Company, Inc.), Ixan® or Diofan® (Solvay Advanced Polymers, LLC), Daran® (Owensboro Specialty Polymers), Vycar® (Lubrizol Advanced Materials, Inc.), and Kynar® (Arkema). This listing is included as examples and is not to be considered exclusive of similar or related polymers or copolymers, or of other polymers or copolymers that may be usefully employed within the scope of the present disclosure.

PVDF and PVDC are especially desirable carbon source polymers because upon pyrolysis they yield non-graphitizing hard carbons comprising high surface area within narrow slit-shaped micropores which have been demonstrated to have tunable pore width useful for molecular sieving behavior. The polyvinylidene fluoride or polyvinylidene chloride raw material source may also contain other additives or processing aids in low concentrations as necessary in order to achieve the desired handling characteristics without detriment to the porosity in the resulting carbon pyrolyzate.

The carbon pyrolyzate adsorbent comprises micropores that are "tunable" via an activation process, e.g., a process of controlled environment, pressure, temperature, and time, to improve selectivity of carbon dioxide adsorption in preference to methane adsorption, as compared to a pyrolyzate that is not processed by such activation process.

In specific embodiments, the carbon pyrolyzate adsorbent may be derived from a polymer or copolymer comprising greater than 50% by weight polyvinylidene chloride, preferably >60% PVDC, and most preferably >70% PVDC, up to 100% PVDC. The polymer or copolymer formulation may optionally include up to 15% by weight, e.g., from 0.1% to 15% by weight, based on the total weight of the formulation, of other additives or processing aids as necessary or desirable for material forming and handling without detriment to the porosity characteristics of the resulting carbon pyrolyzate adsorbent. In various embodiments, the starting polymer or copolymer may have a density in a range of from 0.75 to 1.75 g/cc, and a melting point in a range of from 125° C. to 265° C.

The disclosure further contemplates an apparatus for removing carbon dioxide from a gas mixture including carbon dioxide and methane. Such apparatus may comprise, in specific implementations, at least one adsorbent bed of carbon pyrolyzate adsorbent that is selective for carbon dioxide in contact with the gas mixture. The carbon pyrolyzate adsorbent may be of any suitable character, having any of the characteristics herein described, and may for example have a carbon dioxide adsorbent capacity at 1 bar pressure of greater than 50 cm$^3$ carbon dioxide per gram of adsorbent, a methane adsorption capacity at 1 bar pressure of less than 35 cm$^3$ methane per gram of adsorbent, and a bulk density of greater than 0.55 gram per cubic centimeter of volume.

The at least one adsorbent bed may be arranged, in specific embodiments, for (i) contacting with the gas mixture during a first period of time to adsorb carbon dioxide on the carbon pyrolyzate adsorbent in the bed, and discharge from the bed a carbon dioxide-reduced methane gas, and (ii) desorbing previously adsorbed carbon dioxide from the carbon pyrolyzate adsorbent in the bed during a second period of time.

For the purpose of carrying out such adsorption process, each of the at least one adsorbent bed may be disposed in an adsorber vessel through which the gas mixture is arranged to flow during the first period of time, and which is arranged for desorption of carbon dioxide from the carbon pyrolyzate adsorbent in the bed during the second period of time. The apparatus may for example comprise two or more adsorber vessels, arranged for cyclic alternating and repetitive operation in which one or more of the adsorber vessels is(are) adsorbing carbon dioxide from the gas mixture on the carbon pyrolyzate adsorbent bed therein, while the other(s) of said adsorber vessels is(are) desorbing previously adsorbed carbon dioxide from the carbon pyrolyzate adsorbent bed therein, or in a pressure balancing or standby operation mode awaiting resumption of adsorbing operation.

Thus, each of the at least one adsorbent bed(s) may be disposed in an adsorber vessel through which the gas mixture is arranged to flow during the first period of time, and which is arranged for desorption of carbon dioxide from the carbon pyrolyzate adsorbent in the bed during the second period of time. Vessels may be manifold together with inlet and outlet manifolds each of which is valved and arranged for corresponding operation in which one vessel is on-stream while the other(s) is(are) off-stream, being regenerated or in standby condition awaiting renewal of the on-stream operation, so that each of the multiple vessels progresses through a cycle in an alternating, repeating manner.

For example, the adsorption system apparatus may comprise two adsorber vessels, arranged for cyclic alternating and repetitive operation in which one of the adsorber vessels is adsorbing carbon dioxide from the gas mixture on the carbon pyrolyzate adsorbent bed therein, while the other of said adsorber vessels is desorbing previously adsorbed carbon dioxide from the carbon pyrolyzate adsorbent bed therein, or is in standby operation awaiting resumption of adsorbing operation.

The multiple vessels may be configured and arranged for any suitable cyclic operation. For example, they may be configured and arranged for pressure or vacuum swing operation, temperature swing operation, pressure/vacuum swing operation, or temperature/pressure swing operation. The carbon pyrolyzate adsorbent in the respective beds in the adsorption system apparatus can be of any suitable character as described above for the adsorbent of the present disclosure. Additionally, cascading bed or falling bed approaches are also contemplated as a part of this disclosure.

The adsorbent of the present disclosure is usefully employed for removing carbon dioxide from a gas mixture including carbon dioxide and methane, by contacting the gas mixture with a carbon pyrolyzate adsorbent of the disclosure, e.g., a carbon pyrolyzate adsorbent having a carbon dioxide adsorbent capacity at 1 bar pressure of greater than 50 cm$^3$ carbon dioxide per gram of adsorbent at 273K, a methane adsorption capacity at 1 bar pressure of less than 35 cm$^3$ methane per gram of adsorbent at 21° C., and a bulk density of greater than 0.55 gram per cubic centimeter of volume.

The adsorbent in any of the above-described apparatus and methods may comprise adsorbent of any specific character within the broad scope of the present disclosure. Such adsorbent is highly effective to exclude methane while adsorbing carbon dioxide, and can be utilized in a wide variety of applications in which such methane exclusion/carbon dioxide adsorption is useful for separation and purification purposes. Examples include, without limitation, biogas upgrading, natural gas purification, coal bed methane, and refining operations applications.

Referring now to the drawings, FIG. 1 is a schematic representation of a process system 10 for adsorptive removal of carbon dioxide from a methane/CO$_2$ mixture, utilizing the carbon pyrolyzate adsorbent of the present disclosure.

As illustrated, a methane/$CO_2$ gas mixture, e.g., at 50 psi or other suitable pressure, is introduced to the system in a feed line 12 and flows to the surge vessel 14 ("Natural Gas Receiver"), which provides a buffering vessel to accommodate variations in volumetric flow rate of the influent gas mixture. From the surge vessel 14, the influent gas mixture flows in line 16 to the feed manifold 24 of the carbon dioxide removal system 18. The carbon dioxide removal system 18 comprises adsorbent beds in adsorber vessels 20 and 22. The adsorber vessels are manifolded to one another, at their inlet ends, by feed manifold 24 containing flow control valves 26 and 28, feed/discharge lines 30 and 32, and carbon dioxide extraction manifold 34 containing flow control valves 36 and 38, and at their outlet ends, by a discharge manifold 50 containing flow control valves 52 and 54, flow equalization manifold 44 containing flow control valves 46 and 48, and feed/discharge lines 40 and 42.

Joined to the carbon dioxide extraction manifold 34 is a carbon dioxide discharge line 66 coupled to vacuum pump 68, which in turn discharges the vacuum pumped carbon dioxide in discharge line 70 to the carbon dioxide storage vessel 72. The carbon dioxide storage vessel 72 has a carbon dioxide effluent line 74. Carbon dioxide storage vessel 72 may be replaced by a scrubber or abatement system or by another process for which the CO2 is a feed stream, or the carbon dioxide may be compressed for storage and transport, or may be purged to atmosphere or flared, or other suitable disposition.

The process system 10 also includes a methane discharge line 56 joined to discharge manifold 50 for flowing the carbon dioxide-reduced gas (methane gas) to the "Methane" Receiver 58, which serves as a surge tank for the carbon dioxide-reduced gas received from the carbon dioxide removal system 18. The "Methane" Receiver tank 58 is arranged to discharge carbon dioxide-reduced gas in line 60.

The product carbon dioxide-reduced gas may be flowed to a downstream use or other disposition facility, such as a chemical synthesis facility, natural gas pipeline or transport facility, other natural gas-utilizing process facility, or alternatively cycled for further upgrading.

In the carbon dioxide removal system 18, the on-stream one of the adsorber vessels 20 and 22 receives the influent natural gas, and produces carbon dioxide-reduced gas that flows to the surge vessel 58, from which it is discharged from the system.

It will be recognized that the various valves in the inlet and outlet manifolds of the carbon dioxide removal system 18 will be modulated as to their open/closed positions, to effectuate the continuous operation and cyclic alternating adsorption and desorption steps in the respective adsorber vessels. This cyclic operation may be performed by manually switching valves or automatically using programmed logic control and automatic valves and components.

The features and advantages of the disclosure are more fully illustrated by the following non-limiting examples.

EXAMPLE 1

A commercial polyvinylidene chloride copolymer was pyrolyzed, in both bead and pellet form, then activated under varied conditions of atmosphere, pressure, time and temperature as depicted in Table 1 below. The resulting carbon pyrolyzate adsorbent samples were then evaluated for equilibrium methane capacity at 1 bar pressure and 21° C. and for carbon dioxide capacity at 1 bar pressure and 0° C., with the results set out in Table 1.

TABLE 1

| | Sample Name | Sample Form Factor | Set of Activation Conditions | $CH_4$ Capacity @ 21° C. (cc/g) | $CO_2$ Capacity @ 0° C. (cc/g) |
|---|---|---|---|---|---|
| A | E00034-058 | beads | Recipe A | 37 | 95 |
| B | E00034-071C | beads | Recipe B | 40 | 93 |
| C | E00034-87E | beads | Recipe C | 26 | 82 |
| D | ATMI-1151 | Pellet | Recipe D | 5 | 57 |
| E | ATMI-1350 | Pellet | Recipe C-2 | 30 | 87 |
| F | ATMI-1393 | Pellet | Recipe C-3 | 31 | 90 |

The carbon adsorbent prepared via pyrolysis of the selected commercial polyvinylidene chloride (PVDC) copolymer at temperatures above 650° C. is typified by a high carbon dioxide adsorption capacity of approximately 95 cm³ per gram of adsorbent at 1 bar pressure and 0° C. However there is also fairly significant methane adsorption capacity on the order of 40 cm³ per gram of adsorbent at 1 bar pressure and 21° C. For the intended biogas enhancement application, it would be desirable to reduce the methane adsorption while maintaining a high capacity for $CO_2$.

The porosity of pyrolyzate carbon adsorbents derived from PVDC polymers can be altered by treating with an additional activation process step utilizing controlled atmosphere and temperature for a defined length of time. Those knowledgeable in carbon adsorbent preparation and skilled in the art can readily identify recipes to modify the pore size distribution of these carbons by varying activation pressure, atmosphere, temperature, and time. Table 1 shows a series of samples prepared using the same carbon adsorbent resulting from pyrolysis of this particular PVDC copolymer and subsequently activated using varied activation recipes. An iterative treat and test approach was used to identify favorable activation conditions.

Initial activation trials (Samples A and B), showed minimal impact on either methane or $CO_2$ equilibrium adsorption capacities. Sample C was treated in a manner which reduced the $CH_4$ adsorption to ~26 cc/g but retained most of the $CO_2$ capacity. The activation recipe employed for Sample D reduced the methane adsorption capacity of the adsorbent by over 85%, to ~5 cc/g. This is consistent with narrowing or closure of portals to the pores in the adsorbent material to dimensions of approximately 0.38-0.40 nm and lower, sufficient to exclude methane or to limit its diffusion rate. Unfortunately, some of the pores were found to narrow too greatly under the conditions of Sample D (to less than 0.30 nm) such that the capacity for adsorption of carbon dioxide was also restricted. It was hypothesized that conditions between those used for Sample C and Sample D might yield an adsorbent with a nominal pore size of 0.36 nm which would display reduced mobility of the methane molecules into the pore structure with minimal sacrifice of carbon dioxide permeability.

Samples E and F were prepared using recipes to test this hypothesis. Both showed greater selectivity for carbon dioxide over methane in comparison to the non-activated material. Equilibrium methane capacity was reduced by at least 25% to 30 cc/g or less while keeping the $CO_2$ capacity up close to 90 cc/g. It is believed that under dynamic conditions of competing adsorption on this adsorbent from mixtures of methane and carbon dioxide, selectivity would be even better than indicated by the equilibrium adsorption results from neat gases due to favorable kinetics for the $CO_2$ adsorption.

EXAMPLE 2

The data developed in Example 1 prompted the preparation of a carbon pyrolyzate adsorbent from a commercial polyvinylidene chloride copolymer starting material, which was activated under conditions identified through multiple regression analysis of the Table 1 data. The resulting carbon pyrolyzate adsorbent pellet material, identified as sample E00129-080, was then analyzed for adsorption capacity for both methane and carbon dioxide at 20° C.

Figure 2:
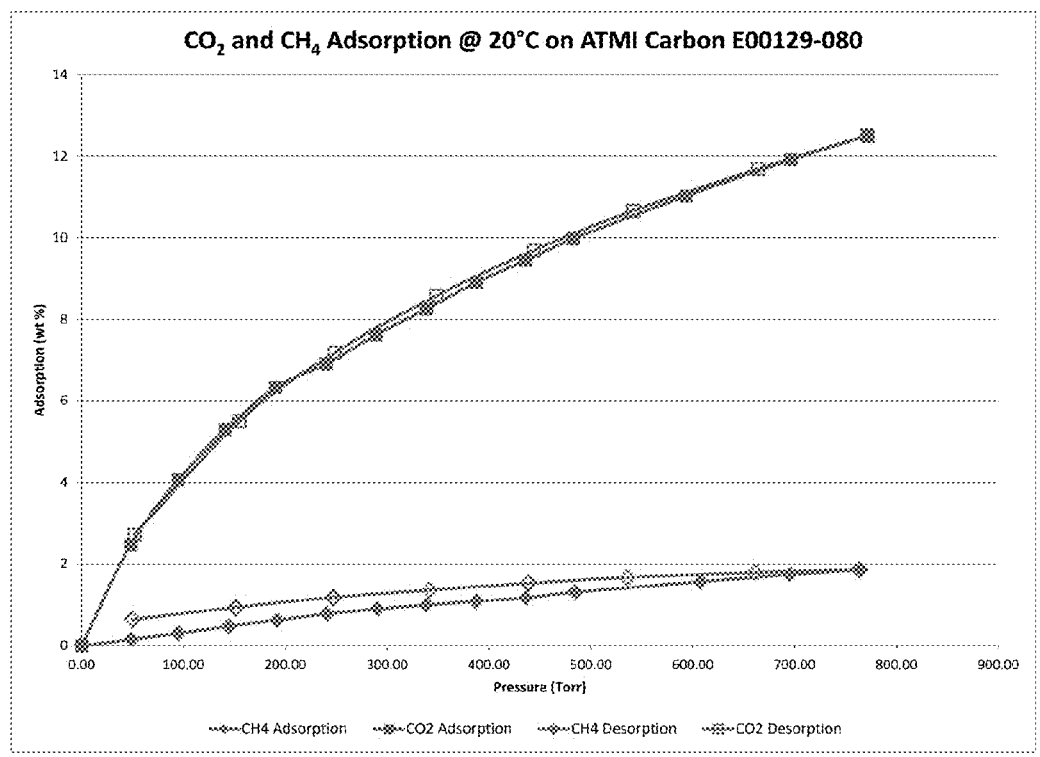
FIG. 2 is a graph of adsorption and desorption isotherms for carbon dioxide and for methane, plotted as adsorption increase, in terms weight of adsorbate as a percentage of the weight of adsorbent, as a function of pressure, in Torr, for a $CO_2$ selective adsorbent of the present disclosure.

The isothermal equilibrium adsorption values in terms of weight of gas adsorbed as a percentage of weight of adsorbent pellets for Sample E00129-080 are shown in FIG. 2. Both $CO_2$ and $CH_4$ adsorption data on this sample at 20° C. are plotted as a function of pressure in Torr. It can be seen that the sample shows a capacity for carbon dioxide adsorption which is greater than six times the capacity for methane at 760 Torr. This plot can also be used to estimate capacities for the two gases under gas mixture conditions. An 80/20 ratio of methane to carbon dioxide in a feed stream at atmospheric pressure would give roughly a $CO_2$ partial pressure of 152 Torr and a $CH_4$ partial pressure of approximately 608 Torr. Looking at the two curves, one can estimate about a 5.5 wt % capacity for $CO_2$ and a 1.6 wt % capacity for $CH_4$ under these conditions which would give nearly a 3.5 times greater capacity for the carbon dioxide. Looking at the desorption isotherms shown in this same plot, one can also see an apparent hysteresis for the methane while the desorption curve for carbon dioxide closely tracks the adsorption curve. This hysteresis effect in the methane isotherm is typically seen in materials that are not reaching thermodynamic equilibrium in a reasonable time and therefore suggests that the $CO_2$, which does reach equilibrium quickly, can move much more freely into and out of the adsorbent than does the $CH_4$. This is further evidence that the pores have been narrowed to a dimension that hinders methane diffusion. As such, one might expect a further kinetic advantage for the $CO_2$ adsorption lending to greater selectivity under non-equilibrium conditions.

The narrowing of pore size accomplished by precision tuning of the activation conditions can yield a carbon structure which impedes or hinders the adsorption of the methane molecules in the gas mixture while still allowing adsorption of the carbon dioxide molecules. The approach takes advantage of the very slightly larger minimum dimension of methane molecule structure (0.38 nm) versus that of the carbon dioxide molecule (0.32 nm) and the unique carbon pyrolyzate adsorbent with tunable slit pores to physically hinder adsorption of the marginally larger molecule.

Figure 3:
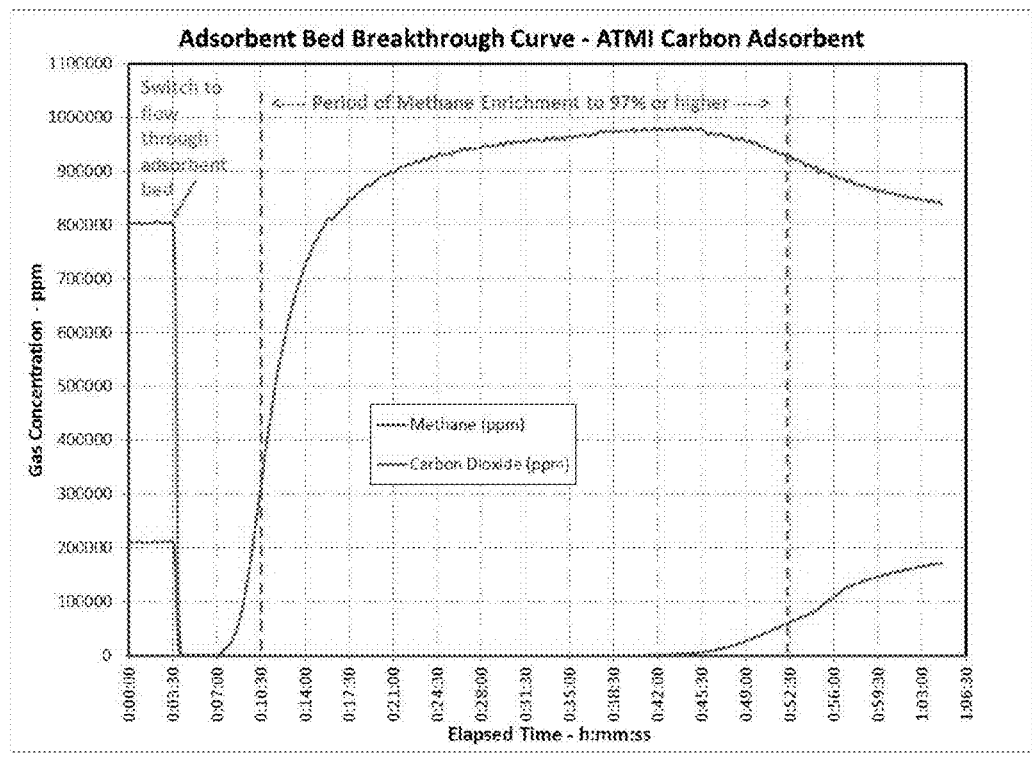
FIG. 3 is a graph of FTIR gas phase analysis data depicting $CO_2$ breakthrough curves across a bed of solid adsorbent according to one embodiment of the present disclosure using a feed mixture of 20% carbon dioxide and 80% methane.

FIG. 3 shows a plot of the dynamic adsorption behavior that one might see from one of the samples listed in Table 1. The data shown represent infrared (FTIR) analysis results on a flowing gas stream as it exits a 12-inch packed adsorbent bed of one of these carbon pyrolyzate samples. The inlet feed gas is an 80% methane, 20% carbon dioxide mixture. At approximately 3.5 minutes, the feed gas is switched from a bypass mode to flow through the bed. The adsorbent immediately captures both the methane and the carbon dioxide and the effluent stream shows no evidence of either gas for approximately 3.5 minutes as the air previously adsorbed on the carbon is replaced. Over the next 7 minutes the methane concentration downstream of the adsorbent bed is building back to its original level while the carbon dioxide is completely adsorbed. Then the test shows exclusively methane in the product stream for about 30 minutes before the $CO_2$ starts to slowly come back. For approximately 42 minutes during the run, the methane concentration is measured to be >33:1 in comparison to the carbon dioxide. This would be an appropriate product gas composition to be eligible to feed back into a natural gas pipeline or be utilized as compressed natural gas for vehicle fuel. The low $CO_2$ concentration would also be advantageous for use in a power generator or combined heat and power schemes. A multiple bed pressure swing adsorption system could utilize such $CO_2$ breakthrough information via a feedback loop and control system for determining the length of ideal adsorption cycle before switching to a regeneration mode for the bed.

Figure 4:
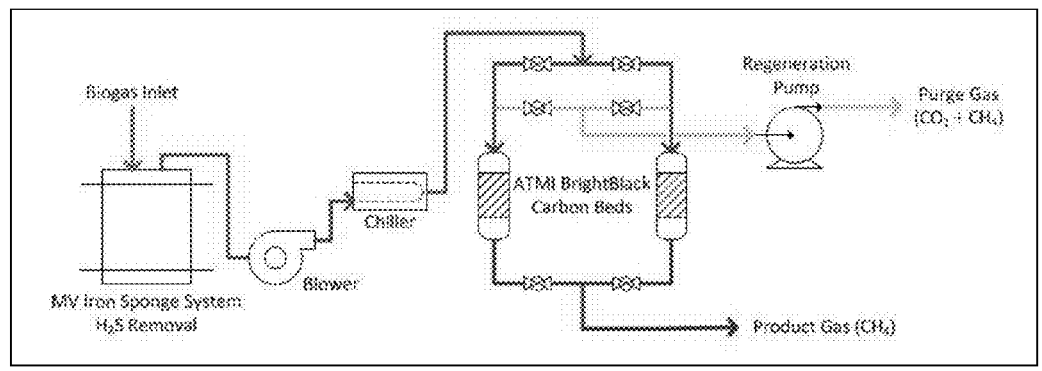
FIG. 4 is a schematic of a simple swing adsorption test system utilized for verification of the utility of adsorbent and method of one embodiment of the present disclosure in the field with an actual biogas mixture feed stream.

Following laboratory analysis of the E00129-080 adsorbent pellets, it was determined that a field trial utilizing this adsorbent in a vacuum/pressure swing adsorption pilot system to upgrade the methane purity from a slipstream of mixed gas coming from an anaerobic digestion plant was desirable. Approximately 15 kg of this pelleted adsorbent was used to fill two carbon beds depicted in FIG. 4. The experimental PSA/VSA system shown in this figure was fed from a biogas stream coming from the anaerobic digester. In this test case, the feed mixture was flowed through an iron sponge scrubber for removal of hydrogen sulfide ($H_2S$) contaminant. The gas at various points in the system was able to be monitored for $CO_2$ content using an infrared (IR) based $CO_2$ monitor able to measure in the range of 0 to 30% $CO_2$ concentration. Inlet and outlet streams were measured constantly for $CO_2$ concentration throughout the testing. The feed stream, following desulfurization by the iron sponge was found to have a fairly constant $CO_2$ concentration of approximately 13.4%. Inlet and outlet flow rates were also monitored throughout the testing using mass flow meters.

Figure 5:
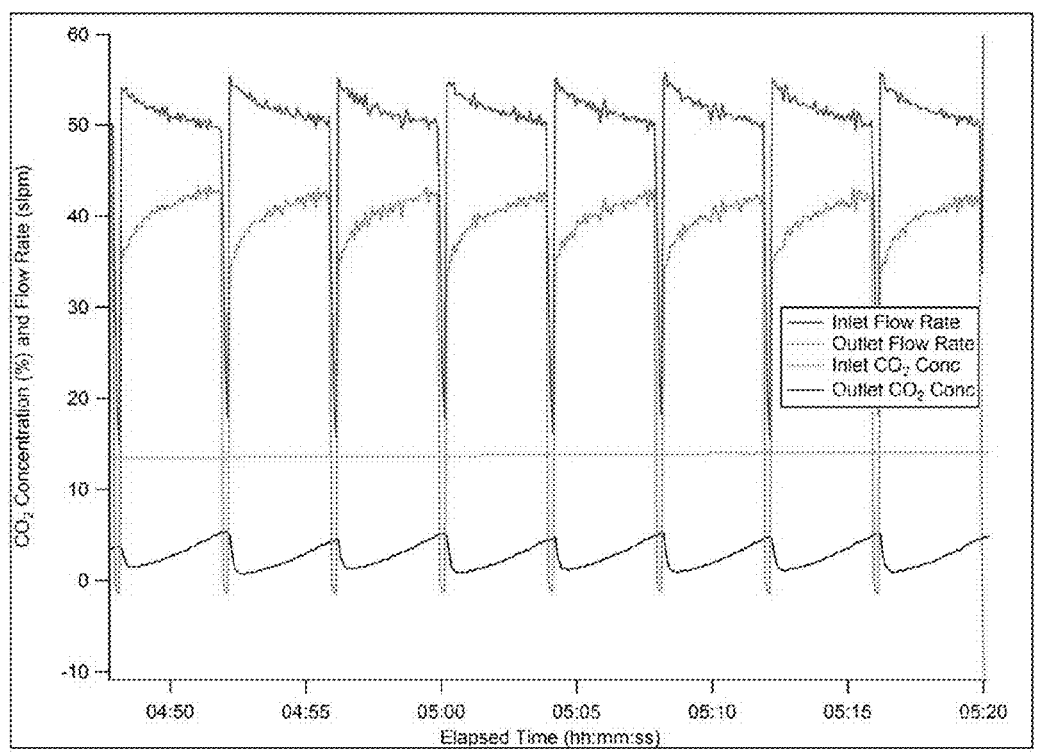
FIG. 5 is a graph of $CO_2$ gas flows and concentrations during field testing of an adsorbent according to one embodiment of the present disclosure, using a biogas feed stream from an anaerobic digester process that is processed in a two bed pressure/vacuum swing adsorption system.

Experiments were conducted to identify the optimal flow rates and cycling times between adsorption and regeneration of the two adsorbent carbon beds to find conditions that would maintain the product methane gas stream to <3% $CO_2$ content. A four minute cycle was identified, and this was run for an extended period of time over a 4 day test period. FIG. 5 shows the operating data obtained over a period of 40 minutes on-line with the swing adsorption system employing a 4 minute cycle. As the feed stream is cycled between adsorbent beds, each cycle shows a brief period of bed charging to atmospheric pressure following the regenerative pump down. The $CO_2$ concentration in the effluent from the refreshed bed is essentially zero and climbs steadily toward 3% until the next switching of beds occurs 4 minutes later. The average $CO_2$ concentration during the testing was approximately 2.7%, giving a methane product purity of roughly 97% or slightly higher. The process was also quite efficient with respect to methane yield. It was calculated that 87 to 90% of the methane entering the system was retained as usable high purity product.

The carbon adsorbent pellet sample used for the aforementioned field trial was analyzed fully in the laboratory. Table 2 contains the data obtained on this carbon material. Ash content of the carbon sample was measured to be less than 0.1% according to ASTM D2866. This purity is important for stable performance in industrial operation for long lifetime materials in a cyclic operation, gas mixture environment. Tapped density of Sample E00129-080 was measured as 0.73 g/cc according to ASTM D2854. Particle density can play a large role in high volumetric adsorption capacity to help keep system size and power requirements minimized. Radial crush strength on the 3.2 mm diameter×2.2 mm thick pellets was measured to be 19 kilopounds according to ASTM D4179. The axial crush strength was found to be too high to be determined using the standard pellet crush strength equipment. It should be noted that this is the crush strength of a binderless pellet. The total composition of the pellets is microporous carbon, and no organic binder material has been added to lend strength at a sacrifice to adsorption capacity. This physical strength of the pellets can prevent crushing and attrition in a deep adsorbent vessel or tall bed configuration. It is the combination of these numerous properties that make the carbon pyrolyzate adsorbent of this embodiment especially attractive for the application of $CO_2$/m and ethane separation.

TABLE 2

| Adsorbent Property | Measure | Target 1 | E00129-080 |
|---|---|---|---|
| Carbon Purity | wt % | >97 | 99.9 |
| Bulk Density | g/cc | 0.55 < X < 1.30 | 0.73 |
| $CO_2$ Adsorption Capacity | cc/g | >50 | 88 |
| $CH_4$ Adsorption Capacity | cc/g | <35 | 28 |
| $CO_2$ Heat of Adsorption | kJ/mole | 5 < X < 50 | 27.2 |
| Single Pellet Radial Crush Strength | kilopond | >7 | 19 |

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A method of removing carbon dioxide from a gas mixture including carbon dioxide and methane, said method comprising contacting said gas mixture with a carbon pyrolyzate adsorbent having a carbon dioxide adsorbent capacity at 1 bar pressure of greater than 50 cm$^3$ carbon dioxide per gram of adsorbent at 273K, a methane adsorption capacity at 1 bar pressure of less than 35 cm$^3$ methane per gram of adsorbent at 21° C., and a bulk density of greater than 0.55 gram per cubic centimeter of volume, wherein said gas mixture comprises gas selected from the group consisting of biogas, natural gas, coal bed methane, refining operations gas, methane fuel gas, and steam-methane reforming gas.

2. The method of claim 1, wherein said carbon pyrolyzate adsorbent has the following characteristics: (i) total ash content of less than 1% as measured by ASTM D2866; (ii) bulk density, as measured by ASTM D2854, of greater than 0.55 g/cc and less than 1.25 g/cc; (iii) carbon dioxide adsorption capacity measured at 1 bar pressure and a temperature of 273 Kelvin of greater than 50 cm3 carbon dioxide per gram of adsorbent; (iv) methane adsorption capacity measured at 1 bar pressure and a temperature of 21° C. of less than 35 cm$^3$ methane per gram of adsorbent; (v) $CO_2$ heats of adsorption and desorption each of which is in the range of 5 to 50 kJ/mole; (vi) single pellet radial crush strength for a nominal 3 mm pellet of greater than 7 kilopound (kP), as measured by ASTM D4179.

3. The method of claim 1, wherein said carbon pyrolyzate adsorbent has a monolith, block, brick, bar, disc, columnar, honeycomb, channeled block, fibrous wool, felt, fabric, sponge, mat, particulate, tablet, pellet, extrudate, or bead form.

4. The method of claim 1, wherein said carbon pyrolyzate adsorbent has a monolithic form.

5. The method of claim 2, wherein said carbon pyrolyzate adsorbent has a monolithic form.

6. The method of claim 1, wherein said carbon pyrolyzate adsorbent has a particulate, tablet, pellet, bead, or extrudate form.

7. The method of claim 1, wherein said carbon pyrolyzate adsorbent has a particulate form.

8. The method of claim 2, wherein said carbon pyrolyzate adsorbent has a particulate form.

9. The method of claim 1, wherein said carbon pyrolyzate adsorbent has a particulate form and comprises carbon pyrolyzate adsorbent particles of particle size in a range of 0.1 to 7.0 mm.

10. The method of claim 1, wherein the carbon pyrolyzate adsorbent comprises a pyrolyzate of a polymer or copolymer, selected from the group consisting of polyvinylidene fluoride, polyvinylidene chloride, and copolymers of polyvinylidene fluoride or polyvinylidene chloride with any of acrylonitrile, styrene, methyl acrylate, vinyl fluoride, vinyl chloride, and methyl methacrylate.

11. The method of claim 1, wherein the carbon pyrolyzate adsorbent comprises a polymer or copolymer of polyvinylidene fluoride.

12. The method of claim 1, wherein the carbon pyrolyzate adsorbent comprises a polymer or copolymer of polyvinylidene chloride.

13. The method of claim 1, wherein the carbon pyrolyzate adsorbent comprises a copolymer of (i) polyvinylidene chloride and (ii) methyl acrylate or methyl methacrylate.

14. The method of claim 2, wherein the carbon pyrolyzate adsorbent comprises a polymer or copolymer of polyvinylidene fluoride.

15. The method of claim 2, wherein the carbon pyrolyzate adsorbent comprises a polymer or copolymer of polyvinylidene chloride.

16. The method of claim 2, wherein the carbon pyrolyzate adsorbent comprises a copolymer of (i) polyvinylidene chloride and (ii) methyl acrylate or methyl methacrylate.

17. The method of claim 10, wherein the polymer or copolymer has a density in a range of from 0.75 to 1.75 g/cc, and a melting point in a range of from 125 to 265° C.

18. A method of making a carbon pyrolyzate adsorbent that is selective for carbon dioxide in contact with gas mixtures including carbon dioxide and methane, said method comprising pyrolyzing a polymer or copolymer of polyvinylidene fluoride or polyvinylidene chloride to form a pyrolyzate, and activating the pyrolyzate under sufficient conditions of environment, pressure, temperature, and time to yield said carbon pyrolyzate adsorbent, having a carbon dioxide adsorption capacity at 1 bar pressure of greater than 50 cm$^3$ carbon dioxide per gram of adsorbent at 273° K, a methane adsorption capacity at 1 bar pressure of less than 35 cm$^3$ methane per gram of adsorbent at 21° C., and a bulk density of greater than 0.55 gram per cubic centimeter of volume.

19. The method of claim 18, wherein the polymer or copolymer has a bulk density in a range of from 0.75 to 1.75 g/cc, and a melting point in a range of from 125 to 265° C., said polymer or copolymer optionally also having up to 15% by weight other additives or processing aids.

20. A method of enhancing removal of carbon dioxide from a gas mixture including carbon dioxide and methane in a process for such removal, said method comprising supplying for use in said process a carbon pyrolyzate adsorbent having a carbon dioxide adsorbent capacity at 1 bar pressure of greater than 50 cm$^3$ carbon dioxide per gram of adsorbent at 273K, a methane adsorption capacity at 1 bar pressure of less than 35 cm$^3$ methane per gram of adsorbent at 21° C., and a bulk density of greater than 0.55 gram per cubic centimeter of volume, as an adsorbent medium for contacting the gas mixture in said process.

21. The method of claim 1, wherein the carbon pyrolyzate adsorbent includes porosity comprising pores having pore size in a range of from 0.30 nm to 0.40 nm.

22. The method of claim 1, wherein the gas mixture comprises natural gas.

23. The method of claim 1, wherein the gas mixture comprises refining operations gas.

24. The method of claim 18, wherein the carbon pyrolyzate adsorbent includes porosity comprising pores having pore size in a range of from 0.30 nm to 0.40 nm.

25. An adsorbent that is selective for carbon dioxide in contact with gas mixtures including carbon dioxide and methane, said adsorbent having a carbon dioxide adsorption capacity at 1 bar pressure of greater than 50 $cm^3$ carbon dioxide per gram of adsorbent at 273K, a methane adsorption capacity at 1 bar pressure of less than 35 $cm^3$ methane per gram of adsorbent at 21° C., a bulk density of greater than 0.55 gram per cubic centimeter of volume, and porosity comprising pores having pore size in a range of from 0.30 nm to 0.40 nm.

26. The adsorbent of claim 25, having the following characteristics: (i) total ash content of less than 1% as measured by ASTM D2866; (ii) bulk density, as measured by ASTM D2854, of greater than 0.55 g/cc and less than 1.25 g/cc; (iii) carbon dioxide adsorption capacity measured at 1 bar pressure and a temperature of 273 Kelvin of greater than 50 cm3 carbon dioxide per gram of adsorbent; (iv) methane adsorption capacity measured at 1 bar pressure and a temperature of 21° C. of less than 35 $cm^3$ methane per gram of adsorbent; (v) $CO_2$ heats of adsorption and desorption each of which is in the range of 5 to 50 kJ/mole; (vi) single pellet radial crush strength for a nominal 3 mm pellet of greater than 7 kilopound (kP), as measured by ASTM D4179.

27. The adsorbent of claim 25, wherein said adsorbent has a monolithic form.

28. The adsorbent of claim 25, wherein said adsorbent has a particulate, tablet, pellet, bead, or extrudate form.

29. The adsorbent of claim 25, wherein said adsorbent has a particulate form and comprises particles of particle size in a range of 0.1 to 7.0 mm.

30. The adsorbent of claim 25, comprising a pyrolyzate of a polymer or copolymer selected from the group consisting of polyvinylidene fluoride, polyvinylidene chloride, and copolymers of polyvinylidene fluoride or polyvinylidene chloride with any of acrylonitrile, styrene, methyl acrylate, vinyl fluoride, vinyl chloride, and methyl methacrylate.

31. An apparatus for removing carbon dioxide from a gas mixture including carbon dioxide and methane, said apparatus comprising at least one adsorbent bed of adsorbent having a carbon dioxide adsorption capacity at 1 bar pressure of greater than 50 $cm^3$ carbon dioxide per gram of adsorbent at 273K, a methane adsorption capacity at 1 bar pressure of less than 35 $cm^3$ methane per gram of adsorbent at 21° C., a bulk density of greater than 0.55 gram per cubic centimeter of volume, and porosity comprising pores having pore size in a range of from 0.30 nm to 0.40 nm, and the at least one adsorbent bed being arranged (i) for contacting with the gas mixture during a first period of time to adsorb carbon dioxide on said carbon pyrolyzate adsorbent in the bed, and discharge from the bed a carbon dioxide-reduced methane gas, and (ii) for desorbing previously adsorbed carbon dioxide from the carbon pyrolyzate adsorbent in the bed during a second period of time.

32. The apparatus of claim 31, wherein each of the at least one adsorbent bed(s) is disposed in an adsorber vessel through which the gas mixture is arranged to flow during the first period of time, and which is arranged for desorption of carbon dioxide from the carbon pyrolyzate adsorbent in the bed during the second period of time.

33. The apparatus of claim 32, comprising two or more adsorber vessels, arranged for cyclic alternating and repetitive operation in which one or more of said adsorber vessels is(are) adsorbing carbon dioxide from the gas mixture on the carbon pyrolyzate adsorbent bed therein, while the other(s) of said adsorber vessels is(are) desorbing previously adsorbed carbon dioxide from the carbon pyrolyzate adsorbent bed therein, or in a pressure balancing or standby operation mode awaiting resumption of adsorbing operation.

34. The apparatus of claim 31, wherein each of the at least one adsorber vessels is arranged for pressure or vacuum swing operation, temperature swing operation, pressure/vacuum swing operation, or temperature/pressure swing operation.

* * * * *